United States Patent [19]

Hammonds, Jr. et al.

[11] Patent Number: 5,168,050

[45] Date of Patent: Dec. 1, 1992

[54] MAMMALIAN EXPRESSION OF THE BONE MORPHOGENETIC PROTEIN-2B USING BMP2A/BMP2B FUSION

[75] Inventors: R. Glenn Hammonds, Jr., Berkeley; Anthony J. Mason, Burlingame, both of Calif.

[73] Assignee: Genentech, Inc., South San Francisco, Calif.

[21] Appl. No.: 528,300

[22] Filed: May 24, 1990

[51] Int. Cl.⁵ .................... C12P 21/06; C12P 19/34; C12N 15/00; C12N 7/00; C12N 5/00; C12N 1/22; C12N 1/16

[52] U.S. Cl. ............................ 435/69.1; 536/27; 435/240; 435/326.1; 530/350

[58] Field of Search ............... 536/27; 435/320.1, 69.4, 435/69.1, 252.33, 240.2

[56] References Cited

U.S. PATENT DOCUMENTS 4,877,864 10/1989 Wang et al. ................. 530/324
5,013,649 5/1991 Wang et al. ................. 435/69.1

FOREIGN PATENT DOCUMENTS 0376785 7/1990 European Pat. Off.
WO88/00205 1/1988 World Int. Prop. O.

OTHER PUBLICATIONS

Hammonds et al., Mol. Endocr., 5(1):149-155 (1991).
Dayhoff et al., Meth. in Enzymol., 91:524-545 (1983).
Plessow et al., Biochem. Biophys. Acta, 1089:280-282 (1991).
Koster et al., Mech. Dev., 33:191-200 (1991).
Wozney et al., Science, 242:1528-1534 (1988).
Roberts & Sporn, Handbook of Experimental Pharmacology, Peptide Growth Factors and Their Receptors I, Sporn and Roberts, eds., (Springer-Verlag: Berlin, 1990) pp. 419-472.
Wakefield et al., J. Biol. Chem., 263(16):7646-7654 (1988).
Wakefield et al., Growth Factors, 1:203-218 (1989).
Gray and Mason, Science, 247:1328-1330 (1990).
Brunner et al., J. Biol. Chem., 264(23):13660-13664 (1989).
Wang et al., PNAS USA, 87:2220-2224 (1990).

Primary Examiner—David L. Lacey
Assistant Examiner—Marianne Porta Allen
Attorney, Agent, or Firm—Janet E. Hasak

[57] ABSTRACT

A DNA construct is provided comprising DNA encoding a mature BMP-2 upstream of which is DNA encoding a precursor portion of a mammalian protein other than the BMP-2. Also provided are mammalian expression vectors and hosts containing such a DNA construct and methods for improved expression using such construct.

17 Claims, 5 Drawing Sheets

```
bmp2a    MVAGTRCLLALLLPQVLLGGA--AGLVPELGRRKFA---AASSGRPSSQPSDEVLSEFELRLLSMFGLKQRPTPSRDAVVPPYMLDLYRRHSGQPGSPAPD
           *  * ***** ****    ** ** **  *                * *    *****  ****** ***  ***  *****  * ******   *
bmp2b    MIPGNRMLMVLLCQVLLGGASHASLIPETGKKKVAEIQGHAGGRRSGQSHELLRDFEATLLQMFGLRRRPQPSKSAVIPDYMRDLYRLQSGEEEEQIH bmp2a    HR-L---ERAASRANTVRSFHHEESLEELPETSGKTTRRFFFNLSSIPTEEFITSAELQVFREQMQDALGNNSSFHHRINIYEIIK-PATANSKFPVTSL
          * *   *  **** **  * *   *   *  *   ***  *  **      * *     **  *     * *    ****
bmp2b    STGLEYPERPASRANTVRSFHHEEHLENIPGTSENSAFRFLFNLSSIPENEVISSAELRLFREQVDQGPDWERGR-HRINIYEVMKPPAEVVPGHLITRL bmp2a    LDTRLVNGNASRWESFDVTPAVMRWTAQGHANHGFVVEVAHLEEKQGVSKRHVRISRSLHQDEHSWSQIRPLLVTFGHDGKGHPL--HKREKRQAK-HKQ
         ***** *  **  *         *  **   *   * *     **         **        *     **
bmp2b    LDTRLVHHNVTRWETFDVSPAVLRWTREKQPNYGLAIEVTHLHQTRTHQGQHVRISRSLPQGSGNWAQLRPLLVTFGHDGRGHALTRRRAKRSPKHHSQ bmp2a    RKRLKS-SCKRHPLYVDFSDVGWNDWIVAPPGYHAFYCHGECPFPLADHLNSTNHAIVQTLVNSKIPKACCVPTELSAISMLYLDENEKVVLKNYQD
          *    * * *   **  *******  *******************************  **  ****   *** 
bmp2b    RARKKNKNCRRHSLYVDFSDVGWNDWIVAPPGYQAFYCHGDCPFPLADHLNSTNHAIVQTLVNSSIPKACCVPTQLSAISMLYLDEYDKVVLKNYQE bmp2a    MVVEGCGCR
         *********
bmp2b    MVVEGCGCR
```

BMP2A/2B

```
          10        20        30        40        50        60        70
MVAGTRCLLALLLPQVLLGGAAGLVPELGRRKFAAASSGRPSSQPSDEVLSEFELRLLSMFGLKQRPTPS
                             RR
          80        90       100       110       120       130       140
RDAVVPPYMLDLYRRHSGQPGSPAPDHRLERAASRANTVRSFHHEESLEELPETSGKTTRRFFFNLSSIP
         150       160       170       180       190       200       210
TEEFITSAELQVFREQMQDALGNNSSFHHRINIYEIIKPATANSKFPVTRLLDTRLVNQNASRWESFDVT
         220       230       240       250       260       270       280
PAVMRWTAQGHANHGFVVEVAHLEEKQGVSKRHVRISRSLHQDEHSWSQIRPLLVTFGHDGRGHALTRRR
         290       300       310       320       330       340       350
RAKRSPKHHSQRARKKNKNCRRHSLYVDFSDVGWNDWIVAPPGYQAFYCHGDCPFPLADHLNSTNHAIVQ
         360       370       380       390       400
TLVNSVNSSIPKACCVPTELSAISMLYLDEYDKVVLKNYQEMVVEGCGCR
```

MAMMALIAN EXPRESSION OF THE BONE MORPHOGENETIC PROTEIN-2B USING BMP2A/BMP2B FUSION

BACKGROUND OF THE INVENTION

1. Field of the Invention

This invention relates to an improved method for expressing DNA encoding the bone morphogenetic protein-2 family in mammalian cells.

2. Description of Related Art

The disorders associated with bone loss present major public health problems for Western societies. Osteoporosis alone may affect 20 million Americans in the early years of the next century. Hence, there is wide interest in identifying factors or potential therapeutic agents that inhibit bone loss and stimulate the formation of healthy new bone.

Bone is an extremely complex, but highly organized, connective tissue that is continuously remodeled during the life of an adult by cellular events that initially break it down (osteoclastic resorption) and then rebuild it (osteoblastic formation). This remodeling process occurs in discrete packets throughout the skeleton, i.e., in both cortical bone and trabecular bone. It has recently been reported that mouse bone marrow cells can be stimulated to generate osteoclasts in the presence of parathyroid hormone-related protein or vitamin D. See Akatsu et al., *Endocrinology*, 125: 20–27 (1989); Takahashi et al., *Endocrinology*, 123: 2600–2602 (1988) and Takahashi et al., *Endocrinology*, 123: 1504–1510 (1988).

The currently available therapeutic agents known to stimulate bone formation are fluoride, estrogen, metabolites, and vitamin D. Fluoride clearly increases trabecular bone mass, but questions remain about the quality of the new bone formed, the side effects observed in some patients, whether there are beneficial effects on vertebral fracture rates, and whether increased fragility of cortical bone with subsequent propensity to hip fracture follows.

Another approach is using agents that promote resorption (parathyroid hormone) and then interrupt resorption (calcitonin). One proposed, but not validated, such sequential therapeutic regimen is coherence therapy, where bone metabolic units are activated by oral phosphate administration and then resorption is inhibited by either diphosphonates or calcitonin.

Within the past few years several factors that stimulate osteoblasts have been identified in bone, including transforming growth factor-$\beta$ (TGF-$\beta$), fibroblast growth factor, platelet-derived growth factor, insulin-like growth factor-I, and $\beta$2 macroglobulin.

Other proteins stored in the bone matrix may also be important for bone formation. When demineralized bone was injected into the muscle or subcutaneous tissue of rats, a cascade of events, including chondrogenesis, ensued. Urist, *Science*, 150: 893 (1965). Since the 1960s several investigators have attempted to identify and characterize this activity and have provided an assay for purification of such activity. Reddi and Huggins, *Proc. Natl. Acad. Sci. USA*, 69: 1601–1605 (1972); Sampath and Reddi, *Proc. Natl. Acad. Sci. USA*. 78: 7599–7603 (1981).

This assay served as the basis for purifying several novel proteins from bone in sufficient quantity and purity to provide amino acid sequence information, including osteogenin, a protein of 22 Kd [Sampath et al., *Proc. Natl. Acad. Sci. USA*, 84: 7109 (1987); Luyten et al., *J. Biol. Chem.*, 264: 13377–13380 (1989)] and a glycoprotein called osteoinductive factor [Bentz et al., *J. Cell. Biol.*, 107: 162a (1989)]. See also Wang et al., *Proc. Natl. Acad. Sci.*, 85: 9484–9488 (1988). Based on amino acid sequence data, clones encoding several proteins related by sequence similarity to TGF-$\beta$ were isolated from bovine and human sources. Wozney et al., *Science*, 242: 1528–1534 (1988); PCT WO 88/00205 published Jan. 14, 1988; U.S. Pat. No. 4,877,864 issued Oct. 31, 1989. These latter proteins included BMP-2A (also known as BMP-2), BMP-2B (also known as BMP-4), and BMP-3. The sequence of tryptic peptides from osteogenin match the sequence reported for BMP-3.

The TGF-$\beta$ supergene family includes five distinct forms of TGF-$\beta$ [Sporn and Roberts, in *Peptide Growth Factors and Their Receptors*, Sporn and Roberts, eds. (Springer-Verlag: Berlin, 1990) pp. 419–472], as well as the differentiation factors vgl [Weeks and Melton, *Cell*, 51: 861–867 (1987)] and DPP-C polypeptide [Padgett et al., *Nature*, 325: 81–84 (1987)], the hormones activin and inhibin [Mason et al., *Nature*, 318: 659–663 (1985); Mason et al., *Growth Factors*, 1: 77–88 (1987)], the Mullerian-inhibiting substance, MIS [Cate et al., *Cell*, 45: 685–698 (1986)], the BMPs, and the developmentally regulated protein Vgr-1 [Lyons et al., *Proc. Natl. Acad. Sci. USA*. 86: 4554–4558 (1989)]. The subset BMP-2A and BMP-2B is approximately 75% homologous in sequence to DPP-C and may represent the mammalian equivalent of that protein.

The proteins of the TGF-$\beta$ supergene family are disulfide-linked homo- or heterodimers encoded by larger precursor polypeptide chains containing a hydrophobic signal sequence, a long and relatively poorly conserved N-terminal pro region of several hundred amino acids, a cleavage site (usually polybasic), and a shorter and more highly conserved C-terminal region. This C-terminal region corresponds to the processed mature protein and contains approximately 100 amino acids with a characteristic cysteine motif, i.e., the conservation of seven of the nine cysteine residues of TGF-$\beta$ among all known family members. Although the position of the cleavage site between the mature and pro regions varies among the family members, the C-terminus of all of the proteins is in the identical position, ending in the sequence Cys-X-Cys-X, but differing in every case from the TGF-$\beta$ consensus C-terminus of Cys-Lys-Cys-Ser. Sporn and Roberts, 1990, supra.

The pro region of TGF-B associates non-covalently with the mature TGF-$\beta$ dimer [Wakefield et al., *J. Biol. Chem.*, 263: 7646–7654 (1988); Wakefield et al., *Growth Factors*, 1: 203–218 (1989)], and the pro regions are found to be necessary for proper folding and secretion of the active mature dimers of both TGF-$\beta$ and activin [Gray and Mason, *Science*. 247: 1328–1330 (1990)]. The association between the mature and pro regions of TGF-$\beta$ masks the biological activity of the mature dimer, resulting in formation of an inactive latent form. Latency is not a constant of the TGF-$\beta$ supergene family, since the presence of the pro region has no effect on activin or inhibin biological activity.

A unifying feature of the biology of the proteins from the TGF-$\beta$ supergene family is their ability to regulate developmental processes. Regarding bone formation in vivo, of all the proteins in the TGF-$\beta$ supergene family, the BMPs and TGF-$\beta$ play the most major role.

Recombinant TGF-$\beta$1 has been cloned [Derynck et al., *Nature*, 316:701–705 (1985)] and expressed in Chinese hamster ovary cells [Gentry et al., *Mol. Cell. Biol.*, 7: 3418–3427 (1987)]. Additionally, recombinant human TGF-β2 [deMartin et al., *EMBO J.*, 6: 3673 (1987)], as well as human and porcine TGF-β3 [Derynck et al., *EMBO J.*, 7: 3737–3743 (1988); ten Dijke et al., *Proc. Natl. Acad. Sci. USA*, 85: 4715 (1988)], have been cloned. Expression levels of the mature TGF-β1 protein in COS cells are increased by substituting a serine residue for cysteine residues located in the pro region of the TGF-β1 precursor. Brunner et al., *J. Biol. Chem.*, 264: 13660–13664 (1989).

BMP-2A and BMP-3 have been recombinantly produced in monkey COS-1 cells and Chinese hamster ovary cells by Wozney et al., supra. However, the level of expression of BMP-2A and -2B cDNA is relatively low when the DNA is not amplified. Higher levels of BMP-2A protein expression in CH cells have been obtained by amplification to a high copy number using methotrexate selection of dihydrofolate reductase. Wang et al., *Proc. Natl. Acad. Sci. USA*, 87: 2220–2224 (1990).

Confirmation of the osteogenic activity of BMPs and commercial production thereof depend on the ability to produce useful amounts of active material by recombinant means of expression and development of methods to purify them in an active form. The ability to successfully reconstitute endochondral bone formation remains the standard by which to judge the osteogenic character of candidate factors. The biological activities of BMP-2A, BMP-3, and an unrelated molecule, BMP-1, were originally assessed in an implant model using material expressed in COS cells, resulting in only cartilage formation. Wozney et al., supra. More recently, the partially purified BMP-2A expressed in CHO cells was shown to require a dose of at least 600 ng/implant to induce cartilage and bone formation. Wang et al., 1990, supra. The osteogenic activities of BMP-2B and BMP-3 have not been established.

It is an object of the present invention to provide purified BMP-2B in sufficient quantities to test for its osteogenic activity, and to produce it on a commercial scale.

It is another object to improve the expression levels of BMP-2 DNA in mammalian cells without amplifying the DNA.

It is still another object to achieve higher production of BMP-2 protein than was previously attained at a level of amplification equivalent to that previously employed.

These and other objects will be apparent to those of ordinary skill in the art of molecular biology.

SUMMARY OF THE INVENTION

Accordingly, this invention provides a DNA construct comprising DNA encoding a mature BMP-2 upstream of which is DNA encoding a precursor portion of a mammalian protein other than that of BMP-2. Preferably, the precursor portion has at least 25% amino acid sequence identity to the native precursor portion of the BMP-2 in the region spanning the N-terminus of the BMP-2 precursor to the first cysteine residue in the mature BMP-2.

In another aspect, this invention provides an expression vector comprising the above-described DNA construct and hosts transformed with such a vector.

In a method for expressing DNA encoding a BMP-2 in mammalian cells, this invention also furnishes the improvement which comprises employing as the host the host transformed with the vector described above.

Additionally, this invention provides a method for producing BMP-2 by culturing mammalian host cells transfected with the expression vector described above, the cells being capable of expressing the DNA construct of the vector, and recovering mature BMP-2 from the cells. Preferably, the recovery is from the host cell media (in which case the expression vector contains a signal sequence, whether native to the precursor or BMP-2 or heterologous to the precursor or BMP-2, that directs secretion of the mature BMP-2 to the medium).

The result of this method is dramatically improved expression levels of BMP-2 DNA in mammalian cells over that attainable using the BMP-2 precursor portion that is native to the BMP-2 to be produced.

BRIEF DESCRIPTION OF THE DRAWINGS

FIG. 1 depicts the amino acid sequences and BMP-2A and BMP-2B and indicates the regions of sequence identity by the "*" notation. The junction between the precursor portions and mature portions is shown by a vertical line with two arms.

FIG. 2 depicts the complete amino acid sequence of the chimera of the precursor portion of BMP-2A and the mature region of BMP-2B.

DESCRIPTION OF THE PREFERRED EMBODIMENTS

Definitions

Figure 3A:
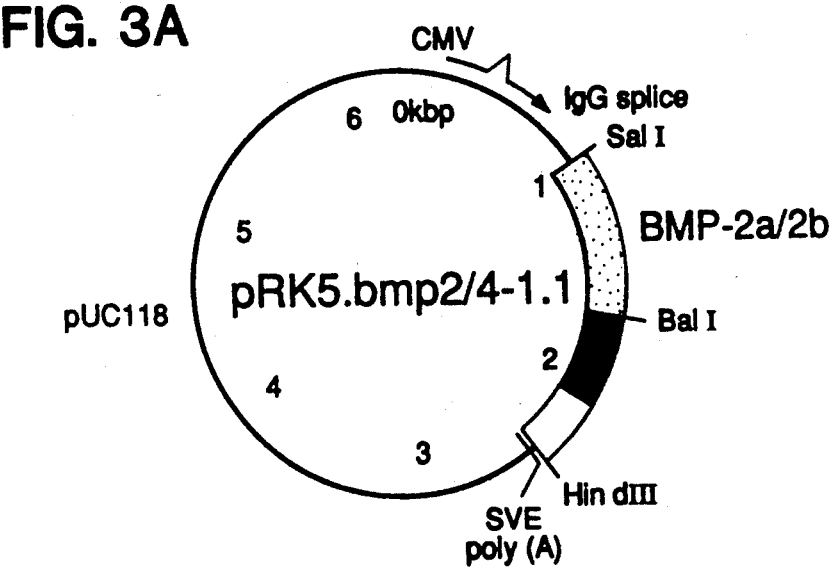
FIG. 3A depicts expression plasmid pRK5.bmp2/4-1.1.

As used herein, the term "BMP-2" refers to the family of bone morphogenetic proteins of the type 2, derived from any species. Reference to BMP-2 herein is understood to be a reference to any one of the currently identified forms, including BMP-2A and BMP-2B (formerly called BMP-4) described by Wozney et al., supra, WO 88/00205, supra, the sequences of which are shown in FIG. 1, as well as to BMP-2 species identified in the future. The term "BMP-2" also includes polypeptides derived from the sequence of any known BMP-2 whose mature sequence is at least about 75% homologous with the sequence of a mature BMP-2, including DPP-C. Members of the BMP-2 family appear to be encoded as a larger precursor that shares a region of high homology near the N-terminus.

As used herein, "precursor portion" refers to the polypeptide sequence derived from a prepro-mammalian protein representing either the pro-domain or prepro-domain without the mature protein. Candidate mammalian proteins having such precursor portions are those encoded as larger precursors that typically contain a signal sequence at their N-terminus followed by a dibasic amino acid cleavage site and a pro-region, followed by another dibasic amino acid cleavage site and the mature region of the protein. Thus, the precursor portion is that which is N-terminal to the mature N-terminus of the mammalian protein and may include the signal sequence for secretion of that protein. Preferably, the mammalian protein from which the precursor portion is derived is a member of the TGF-β supergene family, as described above. Examples of suitable precursor portions are those wherein the signal sequence is followed by a sequence that represents a polypeptide region that after cleavage reassociates with the mature protein covalently or non-covalently, as in the case of insulin, relaxin, inhibin, activin, and TGF-β.

The expression "at least 25% amino acid sequence identity to the native precursor portion of the BMP-2 from the N-terminus of the BMP-2 precursor to the first cysteine residue in the mature region of the BMP-2" refers to a precursor portion that shares this minimum sequence identity to the relevant portion of the BMP-2 DNA being expressed. This sequence identity can be readily calculated for BMP-2A and BMP-2B from the entire amino acid sequences shown in FIG. 1. As examples, the precursor portion of BMP-2A shares 55% amino acid sequence identity to the native precursor portion of BMP-2B from the N-terminus of the BMP-2B precursor to the first cysteine residue in the mature region of the BMP-2B molecule, and vice-versa. The precursor of the protein vgr [Lyons et al., *Proc. Natl. Acad. Sci. USA*, 86: 4554–4558 (1989)], which is related to the product of an amphibian gene vg1 expressed in frog oocytes, shares 25% homology with the relevant portion of BMP-2B. The protein decapenta-plegic gene complex from *Drosophila*, DPP-C [Padgett et al., *Nature*, 325: 81–84 (1987)], shares 27% and 28% amino acid sequence identity with the relevant portions of BMP-2A and BMP-2B, respectively. Most preferred herein is the use of the BMP-2A prepro-domain as the precursor portion for secreting mature BMP-2B.

Modes for Carrying Out the Invention

The vectors and methods disclosed herein are suitable for use for expression in a wide range of mammalian host cell lines.

In general, prokaryotes such as, e.g., *E. coli* strains are preferred for cloning, amplifying, or storing the vectors of interest. Vector DNA is easily obtainable from certain prokaryotes. *E. coli* K12 strain MM 294 (ATCC No. 31,446) is particularly useful for this purpose, as are *E. coli* B and *E. coli* X1776 (ATCC No. 31,537).

In general, plasmid vectors containing replicon and control sequences that are derived from species compatible with the host cell are used in connection with these prokaryotic hosts. The vector ordinarily carries a replication site, as well as marking sequences that are capable of providing phenotypic selection in transformed cells. For example, *E. coli* is typically transformed using pBR322, a plasmid derived from an E. coli species [see, e.g., Bolivar et al., *Gene*, 2: 95 (1977)]. pBR322 contains genes for ampicillin and tetracycline resistance and thus provides easy means for identifying transformed cells. The pBR322 plasmid, or other microbial plasmid or phage, must also contain, or be modified to contain, promoters that can be used by the microbial organism for expression of the selectable marker genes.

Cultures of cells derived from mammalian organisms are useful as expression hosts using tissue culture methods [*Tissue Culture*, Academic Press, Kruse and Patterson, editors (1973)]. Examples of such useful host cell lines include a monkey kidney CVI line transformed by SV40 sequences (COS-7, ATCC CRL 1651); a human embryonic kidney line [293, Graham et al., *J. Gen. Virol.*, 36: 59 (1977)]; baby hamster kidney cells (BHK, ATCC CCL 10); Chinese hamster ovary cells [CHO, Urlaub and Chasin, *Proc. Natl. Acad. Sci. USA*, 77: 4216 (1980)]; mouse sertoli cells [TM4, Mather, *Biol. Reprod.*, 23: 243–251 (1980)]; monkey kidney cells (CVI, ATCC CCL 70); African green monkey kidney cells (VERO-76, ATCC CRL-1587); human cervical carcinoma cells (HELA, ATCC CCL 2); canine kidney cells (MDCK, ATCC CCL 34); buffalo rat liver cells (BRL 3A, ATCC CRL 1442); human lung cells (W138, ATCC CCL 75); human liver cells (Hep G2, HB 8065); mouse mammary tumor cells (MMT 060562, ATCC CCL51); rat hepatoma cells [HTC, M1.54, Baumann et al., *J. Cell. Biol.*, 85: 1–8 (1980)]; and TRI cells [Mather et al., *Annals N.Y. Acad. Sci.*, 383: 44–68 (1982)]. The most preferred mammalian hosts herein are CHO and 293 cell lines.

Expression vectors for such cells ordinarily will contain control regions, which are specific sequences at the 5' and 3' ends of eukaryotic genes that may be involved in the control of either transcription, RNA processing, or translation. At the 3' end of most eukaryotic genes is an AATAAA sequence that signals processing of the mRNA for polyadenylation addition.

Thus, the vector will typically include a promoter located in front of the gene to be expressed, polyadenylation sites, and transcriptional terminator sequences, all described in further detail herein. The vector may optionally also include an origin of replication. Further, the vector may contain, after the promoter, a transcription initiation site located in front of an optional splice unit, which is in turn located before the encoding gene.

One example of a suitable mammalian expression system is that described in copending U.S. Ser. No. 07/441,574 filed Nov. 22, 1989, now abandoned. Briefly, the vector would comprise, in a 5' to 3' direction, a promoter, a start site of transcription, a splice unit, a DNA sequence encoding the BMP-2 hybrid protein, and a polyadenylation region, wherein the splice unit has two or more of the following characteristics:

(a) it comprises no spurious splice sites;
(b) it comprises no spurious ATG codons located upstream of the appropriate ATG start codon of the intron in the splice unit;
(c) its branchpoint sequence comprises the sequence: 5'-YACTGAC, where Y is G, T, or C;
(d) it comprises two or more branchpoint sequences;
(e) its splice donor comprises the sequence: 5'-AGGTXAG, where X is A or G; and
(f) its splice acceptor comprises the sequence: 5'-(Py)$_n$-NPyAGG, where Py is T or C, N is any nucleotide, and n is greater than 5, and (Py)$_n$ can be interrupted by no more than two nucleotides other than Py anywhere within (Py)$_n$.

Other examples of suitable mammalian expression vectors are found in EP 307,247; 260,148; 309,237; and 307,248, the disclosures of which are incorporated herein by reference.

For use in mammalian cells, the control functions on the expression vectors are often provided by viral material. For example, commonly used promoters are derived from the genomes of polyoma, Adenovirus2, retroviruses, cytomegalovirus, and Simian Virus 40 (SV40). Other promoters are those from heterologous sources, e.g., the beta actin promoter. The early and late promoters of SV40 virus are particularly useful because both are obtained easily from the virus as a fragment that also contains the SV40 viral origin of replication [Fiers et al., *Nature*, 273: 113 (1978)]. Smaller or larger SV40 fragments may also be used, provided there is included the approximately 250-bp sequence extending from the HindIII site toward the BglI site located in the viral origin of replication. The immediate early promoter of the human cytomegalovirus is conveniently obtained as a HindIII restriction fragment. Greenaway et al., Gene, 18: 355-360 (1982). Further, it is also possible, and often desirable, to utilize promoter or control sequences normally associated with the desired gene sequence, provided such control sequences are compatible with the host cell systems.

Transcription of a DNA encoding a desired heterologous polypeptide by higher eukaryotes is increased by inserting an enhancer sequence into the vector. The enhancer is a cis-acting element of DNA, usually about from 10 to 300 bp, that acts on a promoter to enhance its transcription-initiation activity. Enhancers are relatively orientation and position independent, having been found 5' [Laimins et al., *Proc. Natl. Acad. Sci. USA*, 78: 993 (1981)] and 3' [Lusky et al., *Mol. Cell Bio.*, 3: 1108 (1983)] to the transcription unit, within an intron [Banerji et al., *Cell*. 33: 729 (1983)] as well as within the coding sequence itself [Osborne et al., *Mol. Cell Bio.*, 4: 1293 (1984)]. Preferably, however, the enhancer element is located upstream of the promoter sequence for this invention. Many enhancer sequences are now known from mammalian genes (globin, elastase, albumin, α-fetoprotein, and insulin). Typically, however, one will use an enhancer from a eukaryotic cell virus. Examples include the SV40 enhancer on the late side of the replication origin (bp 100-270), the cytomegalovirus early promoter enhancer, the polyoma enhancer on the late side of the replication origin, and adenovirus enhancers. One preferred enhancer is the SV40 enhancer region.

Expression vectors used in mammalian host cells will also contain polyadenylation sites. Examples of polyadenylation regions are those derived from viruses such as, e.g., the SV40 (early and late) or HBV.

An origin of replication may be provided either by construction of the vector to include an exogenous origin, such as may be derived from SV40 or other viral (e.g., Polyoma, Adeno, VSV, BPV) source, or may be provided by the host cell. If the vector is integrated into the host cell chromosome, the latter is often sufficient.

The expression vectors may suitably contain a selection gene, also termed a selectable marker. A selection gene encodes a protein necessary for the survival or growth of a host cell transformed with the vector. Examples of suitable selectable markers for mammalian cells include dihydrofolate reductase (DHFR), thymidine kinase (TK), or neomycin. When such selectable markers are successfully transferred into a mammalian host cell, the transformed mammalian host cell can survive if placed under selective pressure.

There are two widely used distinct categories of selective regimes. The first category is based on the metabolism of a cell and the use of a mutant cell line that lacks the ability to grow independent of a supplemented medium. Two examples are CHO DHFR. cells and mouse LTK cells. These cells lack the ability to grow without the addition of such nutrients as thymidine or hypoxanthine. Because these cells lack certain genes necessary for a complete nucleotide synthesis pathway, they cannot survive unless the missing nucleotides are provided in a supplemented medium. An alternative to supplementing the medium is to introduce an intact DHFR or TK gene into cells lacking the respective genes, thus altering their growth requirements. Individual cells that were not transformed with the DHFR or TK gene will not be capable of survival in non-supplemented medium. Therefore, direct selection of those cells requires cell growth in the absence of supplemental nutrients.

The second category is dominant selection, which refers to a selection scheme that does not require the use of a mutant cell line. This method typically employs a drug to arrest growth of a host cell. Those cells that have a novel gene would express a protein conveying drug resistance and would survive the selection. Examples of drugs used in dominant selection include neomycin [Southern and Berg, *J. Molec. Appl. Genet.*, 1: 327 (1982)], mycophenolic acid [Mulligan and Berg, *Science*, 209: 1422 (1980)], or hygromycin [Sugden et al., *Mol. Cell. Biol.*, 5: 410-413 (1985)]. The three examples given above employ bacterial genes under eukaryotic control to convey resistance to the appropriate drug, i.e., neomycin (G418 or geneticin), xgpt (mycophenolic acid), or hygromycin, respectively.

Extremely good amounts of polypeptide are produced by transiently transfected cell cultures using the method of this invention. It is also expected that stable transformants would result in higher production levels of the BMP-2 than transformants with the native proBMP-2 sequence. Furthermore, the process herein is expected to enhance production levels further when the cells are cotransfected with a separate vector encoding a secondary coding sequence. One secondary coding sequence comprises dihydrofolate reductase (DHFR) that is affected by an externally controlled parameter, such as methotrexate (MTX), thus permitting control of expression by control of the MTX concentration.

Typical Methodology Employable

Construction of suitable vectors containing the desired coding and control sequences employs standard recombinant techniques. Isolated plasmids or DNA fragments are cleaved, tailored, and religated to form the desired plasmid.

If flush ends are required, the cleaved DNA preparation may be treated for 30 minutes at 37° C. with DNA Polymerase I (Klenow fragment) or T4 DNA polym phenol-chloroform extracted, and ethanol precipitated. 3' protruding ends are removed by the 3' to 5' exonucleolytic activity of either enzyme, and the 5' protruding ends are made flush by the 5' to 3' polymerase activity incorporating complementary nucleotides until the end of the fragment is reached.

Size separation of the cleaved fragments may be performed using 6 percent polyacrylamide gel described by Goeddel et al., *Nucleic Acids Res.*. 8: 4057 (1980).

For analysis to confirm correct sequences in plasmids constructed, the ligation mixtures are typically used to transform *E. coli* K12 strain 294 (ATCC 31,446) or other suitable *E. coli* strains, and successful transformants selected by ampicillin or tetracycline resistance where appropriate. Plasmids from the transformants are prepared and analyzed by restriction mapping and/or DNA sequencing by the method of Messing et al., *Nucleic Acids Res.*, 9: 309 (1981) or by the method of Maxam et al., *Meth. Enzym*, 65: 499 (1980).

If amplification of the sequences is desired, DHFR-protein-coding DNA sequences are introduced into the mammalian cell host and stable transfectants are selected in the medium. The host cell cultures are grown in the presence of approximately 200–500 nM concentrations of methotrexate, a competitive inhibitor of DHFR activity. The effective range of concentration is highly dependent, of course, upon the nature of the DHFR gene and the characteristics of the host. Clearly, generally defined upper and lower limits cannot be ascertained. Suitable concentrations of other folic acid analogs or other compounds that inhibit DHFR could also be used. MTX itself is, however, convenient, readily available, and effective.

In order to simplify the examples and claims, certain frequently occurring methods will be referenced by shorthand phrases.

"Transfection" refers to the taking up of an expression vector by a host cell whether or not any coding sequences are in fact expressed. Numerous methods of transfection are known to the ordinarily skilled artisan, for example, $CaPO_4$ and electroporation. Successful transfection is generally recognized when any indication of the operation of this vector occurs within the host cell.

"Transformation" means introducing DNA into an organism so that the DNA is replicable, either as an extrachromosomal element or by chromosomal integrant. Depending on the host cell used, transformation is done using standard techniques appropriate to such cells. The calcium treatment employing calcium chloride, as described by Cohen, S.N. *Proc. Natl. Acad. Sci.* (USA), 69: 2110 (1972); Mandel et al., *J. Mol. Biol.* 53:154 (1970); and more recently Liljestrom et al., *Gene*, 40: 241–246 (1985), is generally used for prokaryotes or other cells that contain substantial cell-wall barriers. For mammalian cells without such cell walls, the calcium phosphate precipitation method of Graham and van der Eb, *Virology*, 52: 456–457 (1978) is preferred. General aspects of mammalian cell host system transformations have been described by Axel in U.S. Pat. No. 4,399,216 issued Aug. 16, 1983. Transformations into yeast are typically carried out according to the method of Van Solingen, et al., *J. Bact.*, 130: 946 (1977) and Hsiao, et al., *Proc. Natl. Acad. Sci.* (USA) 76: 3829 (1979). However, other methods for introducing DNA into cells such as by nuclear injection or by protoplast fusion may also be used.

"Operably linked" refers to juxtaposition such that the normal function of the components can be performed. Thus, a coding sequence "operably linked" to control sequences refers to a configuration wherein the coding sequence can be expressed under the control of these sequences and wherein the DNA sequences being linked are contiguous and, in the case of a secretory leader, contiguous and in reading phase. For example, DNA for a presequence or secretory leader is operably linked to DNA for a polypeptide if it is expressed as a preprotein that participates in the secretion of the polypeptide; a promoter or enhancer is operably linked to a coding sequence if it effects the transcription of the sequence; or a ribosome binding site is operably linked to a coding sequence if it is positioned so as to facilitate translation. Linking is accomplished by ligation at convenient restriction sites. If such sites do not exist, then synthetic oligonucleotide adaptors or linkers are used in accordance with conventional practice.

"Control sequences" refers to DNA sequences necessary for the expression of an operably linked coding sequence in a particular host organism. The control sequences that are suitable for prokaryotes, for example, include a promoter, optionally an operator sequence, a ribosome binding site, and possibly, other as yet poorly understood sequences. Eukaryotic cells are known to utilize promoters, polyadenylation signals, and enhancers.

"Expression system" refers to DNA sequences containing a desired coding sequence and control sequences in operable linkage, so that hosts transformed with these sequences are capable of producing the encoded proteins. To effect transformation, the expression system may be included on a vector; however, the relevant DNA may then also be integrated into the host chromosome.

As used herein, "cell," "cell line," and "cell culture" are used interchangeably and all such designations include progeny. Thus, "transformants" or "transformed cells" includes the initial transformant and cultures derived therefrom without regard for the number of transfers. It is also understood that all progeny may not be precisely identical in DNA content, due to deliberate or inadvertent mutations. Mutant progeny that have the same functionality as screened for in the originally transformed cell are included. Where distinct designations are intended, it will be clear from the context.

"Plasmids" are designated by a lower case p preceded and/or followed by capital letters and/or numbers. The starting plasmids herein are commercially available, are publicly available on an unrestricted basis, or can be constructed from such available plasmids in accord with published procedures. In addition, other equivalent plasmids are known in the art and will be apparent to the ordinary artisan.

"Digestion" of DNA refers to catalytic cleavage of the DNA with an enzyme that acts only at specific nucleotide sequences in the DNA. Such enzymes are called restriction enzymes, and the sequence for which each is specific is called a restriction site. The various restriction enzymes used herein are commercially available and their reaction conditions, cofactors, and other requirements as established by the enzyme suppliers are used. Restriction enzymes commonly are designated by abbreviations composed of a capital letter followed by other letters representing the microorganism from which each restriction enzyme originally was obtained and then a number designating the particular enzyme. In general, about 1 $\mu$g of plasmid or DNA fragment is used with about 1–2 units of enzyme in about 20 $\mu$l of buffer solution. Appropriate buffers and substrate amounts for particular restriction enzymes are specified by the manufacturer. Incubation of about 1 hour at 37° C. is ordinarily used, but may vary in accordance with the supplier's instructions. After incubation, protein is removed by extraction with phenol and chloroform, and the digested nucleic acid is recovered from the aqueous fraction by precipitation with ethanol. When appropriate, digestion with a restriction enzyme is followed by bacterial alkaline phosphatase-mediated hydrolysis of the terminal 5' phosphates to prevent the two ends of a DNA fragment from "circularizing," or forming a closed loop that would impede insertion of another DNA fragment at the restriction site. Unless otherwise stated, digestion of plasmids is not followed by 5' terminal dephosphorylation. Procedures and reagents for dephosphorylation are conventional [Maniatis et al., *Molecular Cloning: A Laboratory Manual* (New York: Cold Spring Harbor Laboratory, 1982) pp. 133–134].

"Recovery" or "isolation" of a given fragment of DNA from a restriction digest means separation of the digest on polyacrylamide or agarose gel by electrophoresis, identification of the fragment of interest by comparison of its mobility versus that of marker DNA fragments of known molecular weight, removal of the gel section containing the desired fragment, and separation of the gel from DNA. This procedure is known generally. For example, see R. Lawn et al., *Nucleic Acids Res.* 9: 6103–6114 (1981), and D. Goeddel et al., *Nucleic Acids Res.* 8: 4057 (1980).

"Ligation" refers to the process of forming phosphodiester bonds between two double-stranded nucleic acid fragments [T. Maniatis et al., 1982, supra, p. 146]. Unless otherwise provided, ligation may be accomplished using known buffers and conditions with 10 units of T4 DNA ligase ("ligase") per 0.5 µg of approximately equimolar amounts of the DNA fragments to be ligated.

"Preparation" of DNA from transformants means isolating plasmid DNA from microbial culture. Unless otherwise provided, the alkaline/SDS method of Maniatis et al., 1982, supra, p. 90, may be used.

"Oligonucleotides" are short-length, single- or double-stranded polydeoxynucleotides that are chemically synthesized by known methods [such as phosphotriester, phosphite, or phosphoramidite chemistry, using solid-phase techniques such as described in EP Pat. Pub. No. 266,032 published May 4, 1988, or via deoxynucleoside H-phosphonate intermediates as described by Froehler et al., *Nucl. Acids Res.*, 14: 5399–5407 (1986)]. They are then purified on polyacrylamide gels.

The following example is intended to illustrate specific embodiments now known for practicing the invention, but the invention is not to be considered limited thereto.

All literature citations herein are expressly incorporated by reference.

EXAMPLE 1 cDNAs for BMP-2A and BMP-2B were cloned from a human placental cDNA library constructed in lambda gt10 [Ullrich et al., *Nature*, 313: 756–761 (1985)] using oligonucleotide probes based on the human nucleotide sequence [Wozney et al., supra] using standard cloning techniques [Sambrook et al., *Molecular Cloning: A Laboratory Manual*, Second Ed. (Cold Spring Harbor Laboratory, New York, 1989)]. The probes employed were as follows (where the initiator ATG is underlined and the direction from left to right is 5' to 3'):

BMP-2A Probes

CGACCATGGTGGCCGGGACCCGCTGTCTT-
CTAGCGTTGCTGCTTCC-
CCAGGTCCTCCTGGGCGGC GCG (for 5' end)

AATGAAAAGGTTGTATTAAAGAACTAT-
CAGGACATGGTTGT-
GGAGGGTTGTGGGTGTCGC (for 3' end)

BMP-2B Probes

ATGATTCCTGGTAACCGAATGCT-
GATGGTCGTTTTATTATGCCAAGTCCTG-
CTAGGAGGCGCGAG CCATGCTAGTTTG (for 5' end)

CAGGAGATGGTAGTAGAGG-
GATGTGGGTGCCGCTGAGATCAGG-
CAGTCCTTGAGGATAGACAG (for 3' end)

No clones for BMP-3 were found in the human placental cDNA library using a similar approach to that above. Several cell lines were screened for expression of BMP-3 RNA by polymerase chain reaction amplification of the RNA [Mullis et al., *Cold Spring Harbor Symp. Quant. Biol.*, 51: 263–273 (1986)] using oligonucleotide primers based on the human nucleotide sequence [Wozney et al., supra]. One positive cell line, the NCI-H69 human small cell lung carcinoma [Gazdar et al., *Cancer Res.*, 40: 3502–3507 (1980)] was identified. A cDNA library was prepared from the mRNA and screened with oligonucleotide probes using standard techniques (Sambrook et al., supra). The probe sequences were as follows (where the direction from left to right is 5' to 3'):

AGTGTCCCGCAGCGACGCCGGGAGC-
CGACGCGCCGCGCGGGTACCTAGCC (for 5' end)

TACCCTAACATGACAG-
TAGAGTCTTGCGCTTGCAGATAACCTG-
GCAAAGA (for 3' end)

Positive lambda gt10 clones were identified for BMP-2A, BMP-2B, and BMP-3 proteins, and these clones were sequenced. The sequenced clones encoding the BMP-2A and BMP-2B full-length proteins were digested with SalI. The expression vector pRK5 [EP 307,247 published 3/15/89] was also digested with SalI and the gel-isolated large fragment was ligated with the cDNA SalI digests encoding each BMP to create the expression plasmids pRK5.bmp2a and pRK5.bmp2b, for BMP-2A and BMP-2B, respectively.

The sequenced clone encoding the BMP-3 full-length protein was digested with EcoRI. pRK5 was also digested with EcoRI and the gel-isolated large fragment was ligated with the cDNA EcoRI digest encoding BMP-3 to create the expression plasmid pRK5.bmp3.

A human embryonic kidney cell line (293) [Graham et al., supra] was grown to confluence on 60-mm plates in F12:DMEM (1:1) medium (Gibco) containing 10% fetal calf serum (FCS) and transfected with one of the three BMP expression plasmids by the calcium phosphate method [Gorman, *DNA Cloning*, Vol. II (ed. Glover, D.), 1 43–190 (IRL, Oxford, 1985)]. More specifically, 5–10 µg of one of the three BMP plasmid DNAs was mixed with 1 µg of DNA encoding the VA RNA gener [Thimmappaya et al., *Cell*, 31: 543 (1982)] and dissolved in 250 µl of 0.25 M CaCl$_2$. Added to this (dropwise while vortexing) was 250 µl of 50 mM HEPES (pH 7.35), 280 mM NaCl, 1.5 mM NaPO$_4$, and the precipitate was allowed to form for 5–10 min. at 25° C. The suspended precipitate was then added to the cells and allowed to settle for 4–5 hours in the incubator. The medium was then aspirated off, the cell layer was washed with 5 ml of F12:DMEM (1:1), and 0.5 ml of 20% glycerol in phosphate-buffered saline (PBS) was added for 30 sec. A total of 5 ml of F12:DMEM (1:1) containing 10% fetal bovine serum was added, aspirated off, and replenished. 24 to 48 hours later, the 10% fetal bovine serum medium was replaced with serum-free F12:DMEM (1:1) minus cysteine and methionine. The cells were incubated for 2 hours at 37° C. in 5% $CO_2$ in the presence of 200 µCi/ml $^{35}$S-cysteine and 200 µCi/ml $^{35}$S-methionine. Then the cell layers were washed with PBS and F12:DMEM (1:1) containing cysteine, and methionine was added and the cells were allowed to incubate for 5-7 hours. Conditioned medium was then collected, concentrated 5-fold by lyophilization, and loaded on a 15% SDS gel, which was soaked with Enhance® (New England Nuclear) gel scintillation fluid, dried, and exposed to film at −80° C. for 12 hours. Metabolic labeling of the conditioned medium revealed detectable levels of expression that were low as compared with transfections of similar vectors containing activin or TGF-β cDNAs.

Conditioned medium from the cells transfected with BMP-2A, BMP-2B, or BMP-3 was partially purified by heparin-Sepharose chromatography as follows. A 5-ml heparin-Sepharose CL6B (Pharmacia) column was initially equilibrated with 4 M urea, 20 mM TrisCl at pH 7. Then the conditioned medium in 4 M urea, 20 mM TrisCl, pH 7, was loaded on the column. After loading, the fractions were eluted stepwise with 0, 0.1, 0.5 and 2.0 M NaCl in 4 M urea, 20 mM TrisCl, pH 7. The bone-forming activity of the fractions of each step was assessed in vivo by the method of Sampath and Reddi, supra. Both BMP-2A and BMP-2B possessed easily demonstrable activity, but BMP-3 activity was more difficult to demonstrate. Not all transfections gave biologically active material. These data suggest that expression levels of BMP-3 are substantially lower than those of BMP-2A and BMP-2B using native precursors.

Next, the role of the precursor region in the formation and secretion of mature BMP-2B was examined. An expression plasmid containing DNA encoding the N-terminal prodomain of BMP-2A spliced to the C-terminal mature growth factor domain of BMP-2B (the sequence of which is shown in FIG. 2) was assembled. This hybrid BMP-2A/2B construct codes for a protein of 400 amino acids, consisting of residues 1-268 from BMP-2A and residues 277-409 of BMP-2B. The hybrid was assembled from the BMP-2A plasmid (pRK5.bmp2a) by removing the region from the BalI site to the HindIII site and replacing it with the corresponding BalI to HindIII fragment from the BMP-2B plasmid (pRK5.bmp2b).

Figure 3B:
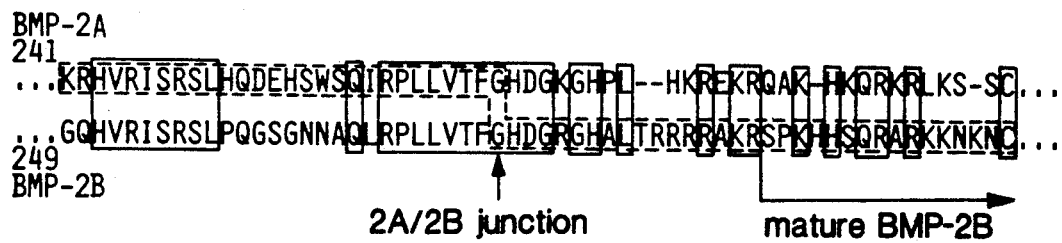
FIG. 3B depicts the junction region of the BMP-2A/2B hybrid insert. A portion of an alignment of BMP-2A and BMP-2B is shown with identical residues boxed. The coding sequence resulting from fusion of BMP-2A and BMP-2B is shaded showing the crossover point. The underlined sequence with an arrow indicates sequence confirmed by Edman degradation of purified recombinant BMP-2B.
Figure 4:
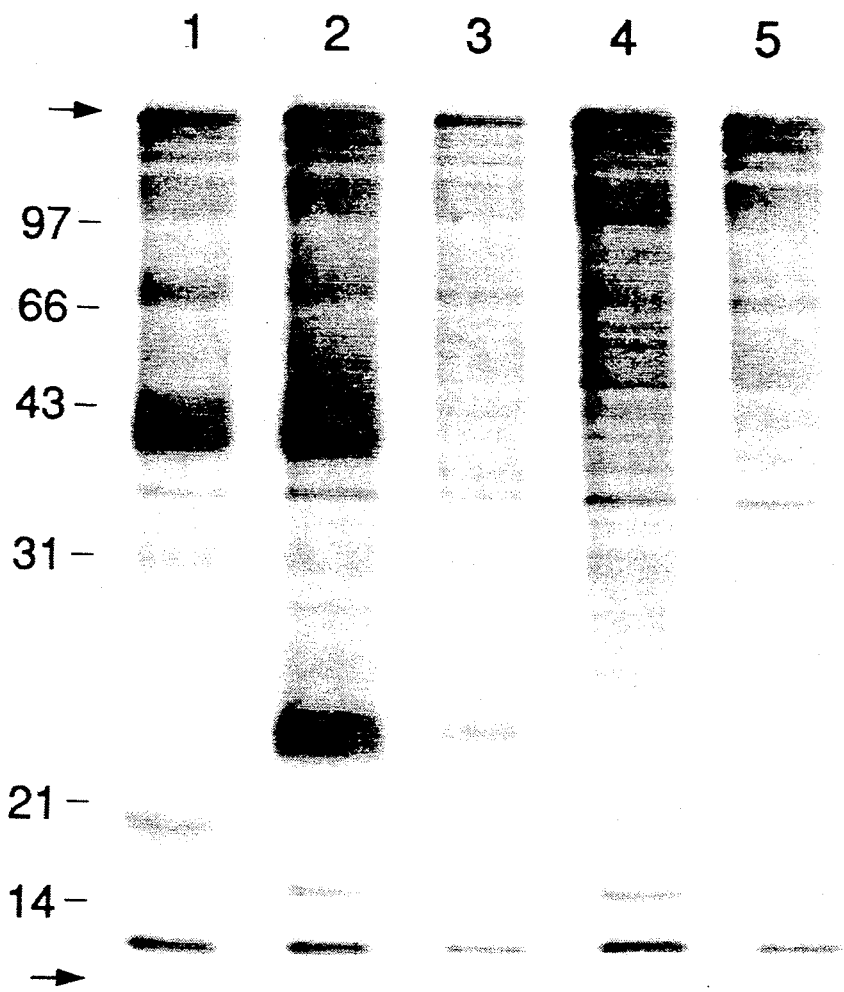
FIG. 4 depicts a fluorogram of an SDS-PAGE reducing gel of supernatants from human embryonic kidney cell line transfections with DNA encoding either the native BMP-2A molecule (lane 1), the chimeric BMP-2A/2B molecule (lane 2), the native BMP-2B molecule (lane 3), control pRK5 plasmid (lane 4), or no plasmid (lane 5).

The resulting expression plasmid (designated pRK5.bmp2/4-1.1) is shown in FIG. 3A. Nucleotide sequencing revealed two difference in the BMP-2A sequence compared to that reported by PCT WO 88/00205, supra: a substitution of A for G at base 261 relative to the ATG start codon, which is silent, and an A for T substitution at base 570 that results in an Arg instead of a Ser at residue 190. (The sequence in FIG. 1 does not reflect the newly found difference at position 190.) The 2A/2B insert sequence is shown in FIG. 3B. E. coli MM294 cells transformed with this plasmid (E. coli MM294/pRK5.bmp2/4-1.1) were deposited with the American Type Culture Collection on May 23, 1990 under ATCC Accession No. 68,330.

pRK5.bmp2/4-1.1, as well as pRK5.bmp2a and pRK5.bmp2b for comparative purposes, were used to transfect 293 cells using the same procedure as described above, and the transfected cells were metabolically labeled using the same procedure as described above, except that they were labeled for four hours with 250 µCi/ml each of the $^{35}$S-labeled methionine and cysteine. They were then applied to a 10% SDS-PAGE gel (reduced) using the procedure described above. FIG. 4 is the fluorogram exposed for 12 hours at −80° C. of this gel (reduced) of conditioned media (5 µl/lane) from the 293 cells transfected with plasmids containing either BMP-2A (lane 1), BMp-2A/2B (lane 2), BMP-2B (lane 3), control pRK5 plasmid (lane 4), or no plasmid (lane 5).

For the hybrid, strong bands were found at 36 kD and 23 kD corresponding to the pro and mature forms, respectively. The full-length BMP-2A construct expressed mostly the 36-kD band of the pro form with a small amount of the 18-kD mature form, while for the full-length BMP-2B construct, only a small amount of the 23-kD mature band was found. Thus, greatly enhanced expression of the DNA encoding the BMP-2B mature dimer was observed over expression with the native prodomains.

Biologically active recombinant BMP-2B homodimers were purified from 3-10 liters of conditioned medium from 293 cultures (in 150-mm dishes) transiently transfected with pRK5.bmp2/4-1.1 and DNA encoding the VA RNA gene (Thimmappaya et al., supra) as described above but using 28 µg pRK5.bmp2/4-1.1 and 8 µg VA gene per dish. One hour after glycerol shock, the medium was replaced with serum-free medium [F12:DMEM (1:1) supplemented with 5 µg/ml human transferrin, 10 µg/ml insulin, and optionally 10 ng/ml epidermal growth factor, Mather, Biol. Reprod., 23: 243 (1980)] (20 ml of media in each plate). The cells were incubated for 24 hours, the medium was harvested, and then fresh medium was added; the cells were incubated again for 24 hours, the medium was harvested and fresh medium was added; and this cycle was repeated once again for a total of three harvests at 24, 48, and 72 hours.

Under the conditions of harvesting, the BMP-2B accumulates in the medium to about 200 ng/ml, while background protein levels remain relatively low, as estimated by the intensity of silver-stained SDS-PAGE gels of the conditioned medium. The protein was purified as follows: A 30-ml heparin-Sepharose CL6B column (Pharmacia) was initially equilibrated with 4 M urea, 20 mM TrisCl at pH 7. Then the conditioned medium in 4 M urea, 20 mM TrisCl, pH 7, was loaded on the column. The fractions were eluted with a 500-ml gradient of 0 to 0.5 M NaCl in 4 M urea, 20 mM TrisCl, pH 7. One major protein band appeared on the SDS-PAGE gel of the pooled fractions, with an estimated 70-80% purity.

The pooled fractions were concentrated with an Amicon Centricon® 10 concentrator about 10-fold, then diluted about 10-fold with 4 M urea, 20 mM Tris, pH 7. The diluted material was loaded onto a 1-ml Pharmacia Mono-Q HR 5/5 column and was eluted with a 0 to 0.3 M NaCl gradient (30 ml) in 4 M urea, 20 mM Tris, pH 7. The peak fractions were pooled, and determined to be about 95% pure by SDS-PAGE. The pooled fractions were dialyzed against 0.1 M acetic acid, lyophilized, and redissolved in 1 ml of 0.1 M acetic acid.

In cases where the purity of the Mono-Q column eluate was judged unsatisfactory, an additional HPLC purification step was 5 employed. This step involved loading the pooled fractions from the Mono-Q column directly on a Vydac C4 RP-HPLC column (100 × 2.1 mm). The HPLC column was eluted with a 30-ml gradient of 0 to 40% N-propanol, 0.1 to 0.06% trifluoroacetic acid. The pooled material from this third step was approximately 95% pure, as judged by SDS gel electrophoresis. This material was lyophilized and redissolved as described above. Final yield of purified mature BMP-2B was determined by quantitative amino acid analysis; the preparation with the three steps yielded 10 μg/liter of conditioned medium, or approximately 5% overall based on SDS gel analysis.

N-terminal amino acid sequencing of the purified mature BMP-2B showed a single amino terminal sequence beginning at residue 285 of BMP-2A/2B (residue 294 of BMP-2B). Sequence data were collected for 18 cycles, and matched exactly that shown underlined in FIG. 3B. No minor sequence was observed. The prominent 36-Kd band observed in the SDS gel of the transfected supernatants was identified as the pro region by amino terminal sequencing after transfer to PVDV membranes. Cleavage of the signal sequence between residues 23 and 24 (. . . LLGGAAG|LVPELGRR-KFAAA) was as predicted by the weight matrix method of von Heijne, *Nucl. Acid Res.*, 144: 683–690 (1986). No cleavage at the nearby RRK sequence was observed.

Recombinant BMP-2B is a disulfide-linked dimer, as shown by a decrease in apparent molecular weight on SDS gel electrophoresis from 33 Kd in the absence of reductants to 23 Kd in the presence of reductants. BMP-2B has two consensus sites for N-glycosylation.

Figure 5A:
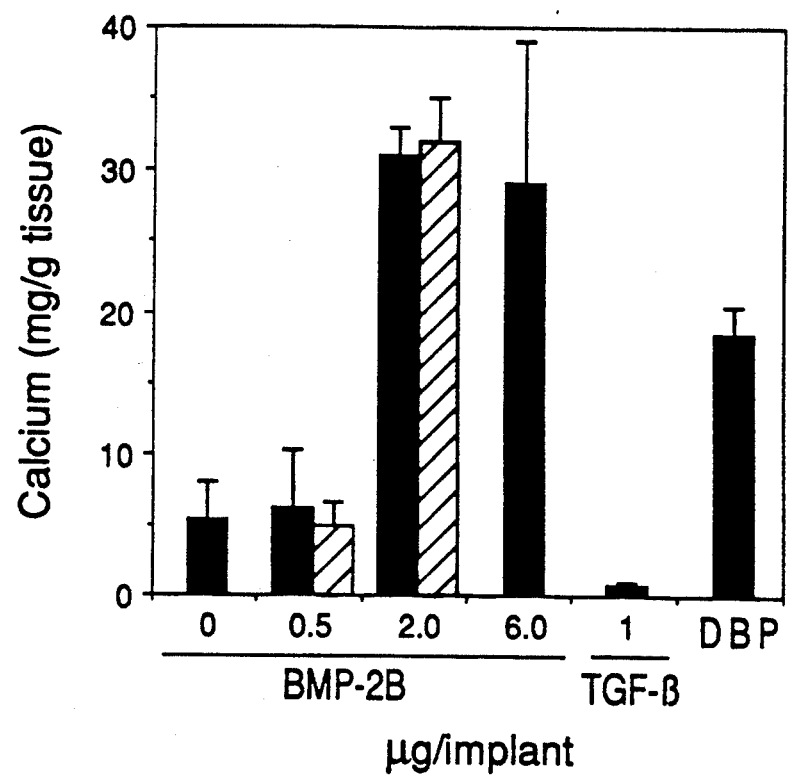
FIG. 5A–B depict graphs of calcium content (FIG. 5A) and alkaline phosphatase content (FIG. 5B) of implants in rats (harvested at 12 days) of demineralized bone powder (DBP) or guanidine-HCl-extracted DBP reconstituted with the indicated amounts of mature recombinant BMP-2B or TGF-β. The solid and cross-hatched bars presented for two doses are duplicate runs.
Figure 5B:
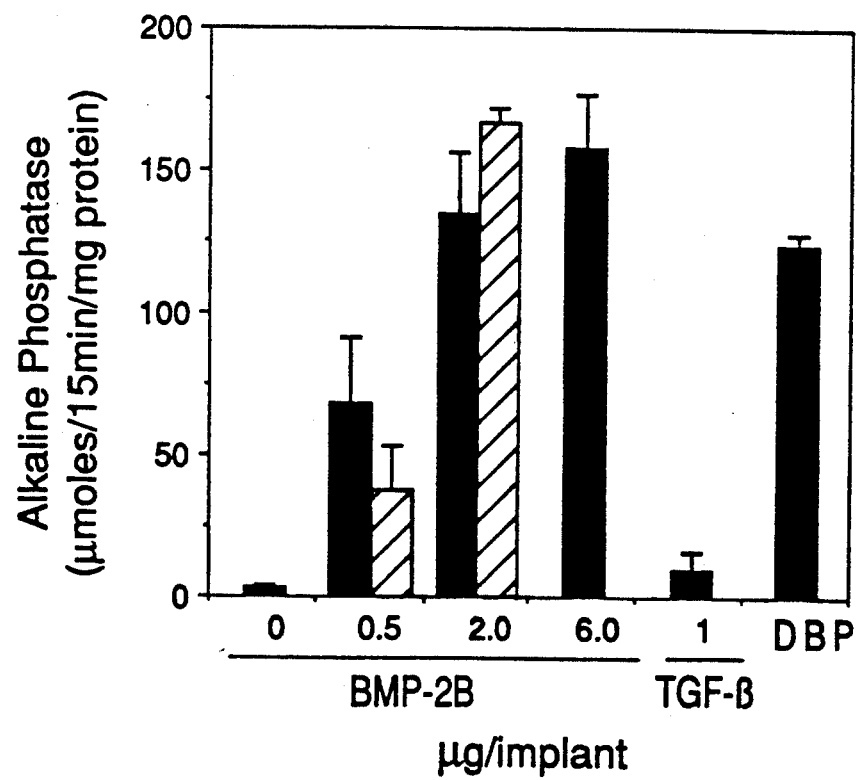

The HPLC-purified recombinant BMP-2B was tested in the bone formation assay of Reddi and Sampath, supra, along with TGF-β and a control. In this assay the implants placed into rats were 25 mg demineralized bone powder (DBP) or 25 mg guanidine-HCl-extracted DBP reconstituted with 0, 0.5, 2.0, or 6.0 μg of the purified recombinant BMP-2B or 1 μg recombinant mature human TGF-β1 (U.S. Pat. No. 4,886,747 issued Dec. 12, 1989). The implants were harvested at 12 days, and the calcium content (FIG. 5A) was measured by atomic absorption spectrophotometry and the alkaline phosphatase content (FIG. 5B) was measured by hydrolysis of p-nitrophenyl phosphate. Duplicate experiments of the 0.5 and 2.0 doses of BMP-2B indicated by solid and cross-hatched bars in FIG. 5 were performed.

A significant increase in calcium content (even over DBP, which contains some BMP) was seen with the 2 μg dose of BMP-2B, while the 0.5 μg dose was sufficient to increase alkaline phosphatase. After a 12-day harvest, implants of guanidine-HCl-extracted DBP alone or reconstituted with 1 μg of purified recombinant BMP-2B were fixed and mounted without decalcification. Three-micron sections were cut and stained with haematoxylin and eosin. Microscopic examination of these stained sections showed abundant bone formation in implants reconstituted with BMP-2B as indicated by the presence of calcium deposits Implants reconstituted with vehicle alone did not form bone.

A construct of the BMP-2A prodomain with the BMP-3 mature region prepared as described above (by replacing the small BalI to HindIII fragment of pRK5.bmp2a with the corresponding BalI-HindIII fragment from pRK5.bmp3) was transfected into 293 cells as described above. In this case, the expression level was no better than the expression levels of the native prosequences for BMP-2A and BMP-3. This experiment shows that the BMP-2A prodomain does not improve expression levels of every member of the entire BMP family, but rather is effective in enhancing expression of DNA encoding the BMP-2 family.

The ability of the heterologous precursor region to improve secretion of the biologically active dimer may reflect a preference of the BMP-2A precursor region for the BMP-2B mature growth factor sequence. It certainly indicates the importance of the precursor region in proper expression and folding of the biologically active mature dimer form in the BMP-2 family.

Deposit of Materials

The following culture has been deposited with the American Type Culture Collection, 12301 Parklawn Drive, Rockville, MD, USA (ATCC):

| Strain | ATCC Dep. No. | Deposit Date |
| --- | --- | --- |
| MM294/pRK5.bmp2/4-1.1 | 68,330 | May 23, 1990 |

This deposit was made under the provisions of the Budapest Treaty on the International Recognition of the Deposit of Microorganisms for the Purpose of Patent Procedure and the Regulations thereunder (Budapest Treaty). This assures maintenance of a viable culture for 30 years from the date of deposit. The organism will be made available by ATCC under the terms of the Budapest Treaty, and subject to an agreement between Genentech, Inc. and ATCC, which assures permanent and unrestricted availability of the progeny of the culture to the public upon issuance of the pertinent U.S. patent or upon laying open to the public of any U.S. or foreign patent application, whichever comes first, and assures availability of the progeny to one determined by the U.S. Commissioner of Patents and Trademarks to be entitled thereto according to 35 USC §122 and the Commissioner's rules pursuant thereto (including 37 CFR §1.14 with particular reference to 886 OG 638).

The assignee of the present application has agreed that if the culture on deposit should die or be lost or destroyed when cultivated under suitable conditions, it will be promptly replaced on notification with a viable specimen of the same culture. Availability of the deposited strain is not to be construed as a license to practice the invention in contravention of the rights granted under the authority of any government in accordance with its patent laws.

The foregoing written specification is considered to be sufficient to enable one skilled in the art to practice the invention. The present invention is not to be limited in scope by the construct deposited, since the deposited embodiment is intended as a single illustration of one aspect of the invention and any constructs that are functionally equivalent are within the scope of this invention. The deposit of material herein does not constitute an admission that the written description herein contained is inadequate to enable the practice of any aspect of the invention, including the best mode thereof, nor is it to be construed as limiting the scope of the claims to the specific illustration that it represents. Indeed, various modifications of the invention in addition to those shown and described herein will become apparent to those skilled in the art from the foregoing description and fall within the scope of the appended claims.

What is claimed is:

1. A DNA construct comprising in the 5' to 3+ direction the DNA sequence for the precursor portion of BMP-2A operably fused to the DNA sequence encoding mature BMP-2B.

2. The DNA construct of claim 1 wherein the BMP-2is human BMP-2B.

3. The DNA construct of claim 1 wherein the precursor portion comprises a signal sequence in addition to its pro-domain.

4. The DNA construct of claim 1 wherein the BMP-2A and BMP-2B are human BMPs.

5. An expression vector comprising the DNA construct of claim 1.

6. An expression vector comprising the DNA construct of claim 4.

7. An expression vector that is pRK5.bmp2/4-1.1.

8. A mammalian host all transformed With the expression vector of claim 5.

9. A mammalian host cell transformed with the expression vector of claim 6.

10. A mammalian host cell transformed with the expression vector of claim 7.

11. An *E. coli* host transformed with the expression vector of claim 7 deposited as ATCC No. 68,330.

12. The host cell of claim 8 that is a 293 human embryonic kidney cell line or Chinese hamster ovary cell line.

13. A method for expressing DNA encoding mature BMP-2B in mammalian host cells, which comprises culturing the host cells of claim 10 under conditions suitable for expression.

14. The host cell of claim 8 that is a 293 human embryonic kidney cell line.

15. A method for expressing DNA encoding mature BMP-2B in mammalian host cells, which comprises culturing the host cells of claim 14 under conditions suitable for expression.

16. A method for expressing DNA encoding mature BMP-2B in mammalian host cells, which comprises culturing the host cells of claim 10 under conditions suitable for expression and recovering mature BMP-2B from the culture.

17. The method of claim 16 wherein the mature BMP-2B is recovered from the culture medium.

* * * * *